United States Patent
Sidhu et al.

(10) Patent No.: US 12,268,642 B2
(45) Date of Patent: Apr. 8, 2025

(54) PERSON SUPPORT APPARATUSES WITH EXIT DETECTION SYSTEMS

(71) Applicant: Stryker Corporation, Kalamazoo, MI (US)

(72) Inventors: Anuj K. Sidhu, Kalamazoo, MI (US); Marko N. Kostic, Oshawa (CA); Michael Joseph Hayes, Kalamazoo, MI (US); Kevin Mark Patmore, Plainwell, MI (US); Sujay Sukumaran, Portage, MI (US)

(73) Assignee: Stryker Corporation, Portage, MI (US)

( * ) Notice: Subject to any disclaimer, the term of this patent is extended or adjusted under 35 U.S.C. 154(b) by 1231 days.

(21) Appl. No.: 17/032,174

(22) Filed: Sep. 25, 2020

(65) Prior Publication Data

US 2021/0007919 A1 Jan. 14, 2021

Related U.S. Application Data

(63) Continuation of application No. 15/266,575, filed on Sep. 15, 2016, now Pat. No. 10,786,408, which is a
(Continued)

(51) Int. Cl.
*A61G 7/018* (2006.01)
*A61B 5/11* (2006.01)
(Continued)

(52) U.S. Cl.
CPC ............ *A61G 7/018* (2013.01); *A61B 5/1115* (2013.01); *A61G 7/005* (2013.01); *A61G 7/012* (2013.01);
(Continued)

(58) Field of Classification Search
CPC ........ A61G 7/002; A61G 7/005; A61G 7/012; A61G 7/015; A61G 7/018; A61G 7/05;
(Continued)

(56) References Cited

U.S. PATENT DOCUMENTS 7,253,366 B2 * 8/2007 Bhai ...................... G16H 40/63
177/144
7,437,787 B2 * 10/2008 Bhai ...................... G16H 40/63
177/144
(Continued)

FOREIGN PATENT DOCUMENTS

AU 2020204399 A1 * 3/2021 ........... A61B 5/1115
AU 2021271022 A1 * 10/2022 ........... A61B 5/1115
(Continued)

*Primary Examiner* — Robert G Santos
(74) *Attorney, Agent, or Firm* — Warner Norcross + Judd LLP

(57) ABSTRACT

A person support apparatus, such as a bed, cot, stretcher, or the like, includes an exit detection system that has, in some embodiments, multiple user-selectable modes. A first mode issues an alert in response to a static condition being met and the second mode issues an alert in response to a dynamic condition being met. The static condition may be defined by an unchanging boundary that triggers an alert if the occupant's center of gravity crosses the boundary. The dynamic condition may be defined by a changing boundary that triggers an alert if the occupant's center of gravity crosses it. The changing boundary may change based upon the occupant's height, weight, BMI, vital sign, or other characteristic. The changing boundary may also change based upon a position of one or more components of the person support apparatus, such as a siderail or Fowler section.

10 Claims, 5 Drawing Sheets

Related U.S. Application Data continuation-in-part of application No. 14/918,003, filed on Oct. 20, 2015, now Pat. No. 10,617,327, and a continuation-in-part of application No. 14/873,734, filed on Oct. 2, 2015, now Pat. No. 10,357,185.

(60) Provisional application No. 62/076,005, filed on Nov. 6, 2014, provisional application No. 62/065,242, filed on Oct. 17, 2014.

(51) Int. Cl.
*A61G 7/005* (2006.01)
*A61G 7/012* (2006.01)
*A61G 7/015* (2006.01)
*A61G 7/05* (2006.01)
*A61G 13/04* (2006.01)
*A61G 13/06* (2006.01)
*A61G 13/08* (2006.01)

(52) U.S. Cl.
CPC ........... *A61G 7/015* (2013.01); *A61G 7/0516* (2016.11); *A61G 13/04* (2013.01); *A61G 13/06* (2013.01); *A61G 13/08* (2013.01); *A61G 2203/32* (2013.01); *A61G 2203/42* (2013.01)

(58) Field of Classification Search
CPC .. A61G 7/0507; A61G 7/0524; A61G 7/0527; A61G 13/02; A61G 13/04; A61G 13/06; A61G 13/08; A61G 2203/32; A61B 5/1115
USPC .............. 5/613, 616–618, 611, 600, 11, 425, 5/428–430; 340/573.1
See application file for complete search history.

(56) References Cited

U.S. PATENT DOCUMENTS

| | | | |
|---|---|---|---|
| 9,875,633 B2 * | 1/2018 | Pirio | A61B 5/1115 |
| 10,276,021 B2 * | 4/2019 | Pirio | A61B 5/6892 |
| 10,357,185 B2 * | 7/2019 | Kostic | A61B 5/6892 |
| 10,617,327 B2 * | 4/2020 | Kostic | A61G 7/018 |
| 10,786,408 B2 * | 9/2020 | Sidhu | A61G 7/018 |
| 11,484,223 B2 * | 11/2022 | Kostic | A61B 5/6892 |
| 11,490,834 B2 * | 11/2022 | Sukumaran | G08B 29/185 |
| 11,800,995 B2 * | 10/2023 | Sukumaran | A61G 7/0509 |
| 12,144,607 B2 * | 11/2024 | Kostic | A61G 7/015 |
| 2006/0028350 A1 * | 2/2006 | Bhai | A61B 5/1115 177/144 |
| 2007/0268147 A1 * | 11/2007 | Bhai | G01G 19/445 340/666 |
| 2016/0078740 A1 * | 3/2016 | Pirio | A61B 5/6892 340/573.4 |
| 2016/0106345 A1 * | 4/2016 | Kostic | A61B 5/1115 5/652 |
| 2016/0128610 A1 * | 5/2016 | Kostic | A61G 7/015 5/613 |
| 2017/0098359 A1 * | 4/2017 | Sidhu | A61G 7/015 |
| 2017/0243459 A9 * | 8/2017 | Sidhu | A61G 7/005 |
| 2018/0108239 A1 * | 4/2018 | Pirio | G08B 21/0461 |
| 2019/0290169 A1 * | 9/2019 | Kostic | A61B 5/1121 |
| 2020/0214599 A1 * | 7/2020 | Kostic | A61G 13/04 |
| 2021/0007919 A1 * | 1/2021 | Sidhu | A61G 7/005 |
| 2021/0052197 A1 * | 2/2021 | Sukumaran | A61B 5/6892 |
| 2021/0353179 A1 * | 11/2021 | Sukumaran | A61G 7/0528 |
| 2023/0067526 A1 * | 3/2023 | Sukumaran | A61G 7/0509 |

FOREIGN PATENT DOCUMENTS

| | | | | |
|---|---|---|---|---|
| CA | 3226912 A1 | * | 4/2016 | ........... A61B 5/1036 |
| CA | 3171373 A1 | * | 11/2021 | ........... A61B 5/1115 |
| EP | 2995242 A1 | * | 3/2016 | ........... A61B 5/1115 |
| EP | 3206654 B1 | * | 11/2020 | ........... A61B 5/1036 |
| EP | 2995242 B1 | * | 11/2023 | ........... A61B 5/1115 |
| WO | WO-2016060862 A1 | * | 4/2016 | ........... A61B 5/1036 |
| WO | WO-2016073186 A1 | * | 5/2016 | ........... A61B 5/1115 |
| WO | WO-2021231674 A1 | * | 11/2021 | ........... A61B 5/1115 |

\* cited by examiner

PERSON SUPPORT APPARATUSES WITH EXIT DETECTION SYSTEMS

CROSS-REFERENCE TO RELATED APPLICATIONS

This application claims priority to U.S. patent application Ser. No. 15/266,575 filed Sep. 15, 2016, now U.S. Pat. No. 10,786,408, by inventors Anuj Sidhu et al. and entitled PERSON SUPPORT APPARATUSES WITH EXIT DETECTION SYSTEMS, which in turn claims priority as a continuation-in-part application of U.S. patent application Ser. No. 14/918,003, filed Oct. 20, 2015, now U.S. Pat. No. 10,617,327, entitled EXIT DETECTION SYSTEM WITH COMPENSATION, which in turn claims priority to U.S. Pat. Appl. Ser. No. 62/076,005, filed Nov. 6, 2014, entitled EXIT DETECTION SYSTEM WITH COMPENSATION. The aforementioned Ser. No. 15/266,575 application also claims priority as a continuation-in-part application of U.S. patent application Ser. No. 14/873,734 filed Oct. 2, 2015, now U.S. Pat. No. 10,357,185, entitled PERSON SUPPORT APPARATUSES WITH MOTION MONITORING, which claims priority to U.S. Pat. Appl. Ser. No. 62/065,242, filed Oct. 17, 2014, entitled PERSON SUPPORT APPARATUSES WITH MOTION MONITORING. The complete disclosures of all of the aforementioned references are incorporated herein by reference.

BACKGROUND

The present disclosure relates to person support apparatuses, such as beds, cots, stretchers, operating tables, recliners, or the like. More specifically, the present disclosure relates to person support apparatuses that include sensors for monitoring the motion and/or activity of an occupant of the person support apparatus and issuing an alert if the occupant is, or may be, about to exit the person support apparatus.

Existing hospital beds and/or stretchers often include an exit detection system that is adapted to detect when a patient has exited the bed, or when a patient may be about to exit the bed. Typically, such beds include circuitry for providing an audio or visual alert when such an exit or pre-exit situation is detected. In many cases, the bed or stretchers include circuitry for transmitting a signal to a remote location, such as a nurses' station, so that the appropriate caregivers are notified of the exit, or pre-exit condition, and can respond appropriately. The exit detection system itself may be implemented in a variety of manners, including using a plurality of force sensors,

SUMMARY

According to various embodiments, an improved person support apparatus is provided that analyzes the motion of an occupant and compares it to one or more conditions or criteria. The conditions or criteria may vary, depending upon user-selected settings. According to some aspects, the conditions or criteria vary in response to one or more characteristics of the occupant, to the position of one or more components of the person support apparatus, to one or more characteristics of the environment of the person support apparatus, and/or to one or more other characteristics. The changing criteria allow improved alerting regarding an occupant's intention to exit the person support apparatus, including, but not limited to, advance notification of such an exit. The monitoring of the occupant's motion may also provide a reduction in false alarms regarding an occupant's intention to exit the person support apparatus.

According to one embodiment of the present disclosure, a person support apparatus is provided that includes a support surface and an exit detection system. The support surface is adapted to support an occupant of the person support apparatus. The exit detection system is adapted to issue an alert if the occupant of the person support apparatus is moving toward exiting the support surface. The exit detection system includes a first mode and a second mode that are selectable by a user. The first mode issues an exit alert based upon a variable parameter meeting a static criterion and the second mode issues an alert based upon the variable parameter meeting a dynamic criterion.

According to other aspects, the variable parameter is a center of gravity of the occupant and the static criterion is met if the center of gravity of the occupant moves outside of a static zone having an unchanging boundary and the dynamic criterion is met if the center of gravity of the occupant moves outside of a dynamic zone having a changing boundary.

The dynamic criterion, in some embodiments, is based upon a vital sign of the occupant or a position of a component of the person support apparatus, such as, but not limited to, a siderail of the person support apparatus or a Fowler section of the person support apparatus. The dynamic criterion may also be based upon the environment in which the patient support apparatus is currently located in.

In some embodiments, the exit detection system includes a plurality of force sensors adapted to detect downward forces exerted by the occupant on the support surface. The exit detection system uses outputs from the force sensors when operating in both the first mode and the second mode.

The exit detection system, when operating in the first mode, may compare a first value derived from outputs of the force sensors to a first threshold, and compare a second value derived from the outputs of the force sensors to a second threshold. The thresholds may further be changed in response to the position of any one or more of the siderails.

The first and second boundaries are boundaries of a zone, in some embodiments. In such embodiments, the exit detection system makes at least one reduction in an area of the zone in response to a first one of the siderails being in the lowered position and makes at least one expansion of the area of the zone in response to the first one of the siderails being in the raised position.

A user selectable mode may also be included. The third mode may take into account a characteristic of the occupant in determining whether or not the occupant is moving toward exiting the support surface. The characteristics of the occupant may be a vital sign of the occupant and/or it may be an assessment of the fall risk of the occupant.

According to another embodiment, a person support apparatus is provided that includes a support surface and an exit detection system. The support surface is adapted to support thereon an occupant of the person support apparatus. The exit detection system is adapted to issue an alert if the occupant of the person support apparatus is moving toward exiting the support surface. The exit detection system takes into account a height of the occupant in determining whether or not the occupant is moving toward exiting the support surface.

According to other aspects, in addition to the height of the occupant, the exit detection system may also take into account one or more vital signs of the occupant, the weight of the occupant, a gender of the occupant, a ratio of the occupant's height and weight, and/or other characteristics of the occupant in determining whether or not the occupant is moving toward exiting the support surface.

In some embodiments, the exit detection includes plurality of load cells adapted to detect a weight of the occupant. The exit detection system may calculate a center of gravity from forces detected by the load cells and determine whether or not the occupant is moving toward exiting the support surface based upon the calculated center of gravity. Alternatively or additionally, the exit detection system may monitor changes in the weight distribution detected by the load cells to determine whether or not the occupant is moving toward exiting the support surface.

In some embodiments, a vital sign of the occupant is detected by processing outputs from the plurality of load cells, while in other embodiments, a vital sign of the occupant is forwarded to the person support apparatus from a vital sign sensor separate from the person support apparatus.

According to another embodiment, a person support apparatus is provided that includes a support surface and an exit detection system. The support surface is adapted to support thereon an occupant of the person support apparatus. The exit detection system is adapted to issue an alert if the occupant of the person support apparatus moves in a manner that meets a set of criteria. The exit detection system changes the set of criteria based upon a vital sign of the occupant of the person support apparatus.

According to other aspects, the exit detection system changes the set of criteria based also upon one or more other factors, such as a height and a weight of the occupant, a position of one or more components of the person support apparatus, a gender of the occupant, the environment of the person support apparatus, a proximity of a caregiver, a time of day, and/or other factors.

According to another embodiment, a person support apparatus is provided that includes a support surface and an exit detection system. The support surface is adapted to support thereon an occupant of the person support apparatus. The exit detection system is adapted to issue an alert if the occupant of the person support apparatus is moving toward exiting the support surface. The exit detection system includes a plurality of user-selectable modes. In a first mode, the exit detection system takes into account a characteristic of the occupant in determining whether or not the occupant is moving toward exiting the support surface. In a second mode, the exit detection system does not take into account the characteristic of the occupant in determining whether or not the occupant is moving toward exiting the support surface.

According to other aspects, the characteristic of the occupant includes one or more of the following: a vital sign of the occupant, a height of the occupant, a weight of the occupant, a gender of the occupant, and a fall risk of the occupant.

The exit detection system may also take into account, in addition to the characteristic of the occupant, a position of the siderails, a height of the support surface, and/or a position of the Fowler section of the person support apparatus.

According to another embodiment, a person support apparatus is provided that includes a support surface, a plurality of siderails, a plurality of siderail sensors, and an exit detection system. The support surface is adapted to support thereon an occupant of the person support apparatus. The siderails are movable between raised and lowered positions. The siderail sensors detect downward forces exerted on the plurality of siderails. The exit detection system is adapted to issue an alert if the occupant of the person support apparatus is moving toward exiting the support surface. The exit detection system includes a plurality of force sensors adapted to detect downward forces exerted by the occupant on the support surface. The exit detection system uses outputs from both the plurality of siderail sensors and the plurality of force sensors when determining whether or not the occupant is moving toward exiting the support surface.

According to other aspects, the exit detection system compares a sum of two or more of the forces detected by the force sensors to a force detected by at least one of the siderail sensors when determining whether or not the occupant is moving toward exiting the support surface. The exit detection system may be configured to determine that the occupant is moving toward exiting the support surface if the force detected by at least one of the siderail sensors increases by more than a threshold amount for more than a threshold time.

In some embodiments, the threshold amount varies based upon a sum of forces detected by the force sensors.

According to another embodiment, a person support apparatus is provided that includes a support surface and an exit detection system. The support surface is adapted to support thereon an occupant of the person support apparatus. The exit detection system is adapted to detect if the occupant of the person support apparatus is moving toward exiting the support surface. The exit detection system presents guidance to the occupant for safely exiting the person support apparatus if the exit detection system detects the occupant is moving toward exiting the support surface.

According to other aspects, the guidance includes aural instructions issued from the person support apparatus.

In some embodiments, the exit detection system includes a plurality of force sensors adapted to detect downward forces exerted by the occupant on the support surface, and the exit detection system presents the guidance to the occupant in response to monitoring how quickly, and/or by how much, outputs from the force sensors change.

The guidance includes, in some embodiments, aural commands to the occupant to slow down his or her movement if the outputs from the force sensors change at a rate greater than a threshold speed.

An occupant control is included in some embodiments. The occupant control communicates with the exit detection system. The exit detection system presents the guidance to the occupant for safely exiting the person support apparatus in response to activation of the occupant control.

In some embodiments, the exit detection system is able to be armed or disarmed and the exit detection system only presents guidance to the user in response to activation of the occupant control if the exit detection system is disarmed. In other embodiments, the exit detection system is automatically disarmed in response to the occupant activating the occupant control.

According to another embodiment, a person support apparatus is provided that includes a support surface, an exit detection system, and an occupant control. The support surface is adapted to support thereon an occupant of the person support apparatus. The exit detection system is adapted to detect if the occupant of the person support apparatus is moving toward exiting the support surface. The occupant control communicates with the exit detection system and presents guidance to the occupant for safely exiting the person support apparatus in response to activation of the occupant control.

In some embodiments, the exit detection system adjusts the guidance presented based upon movement of the occupant, as detected by the exit detection system.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
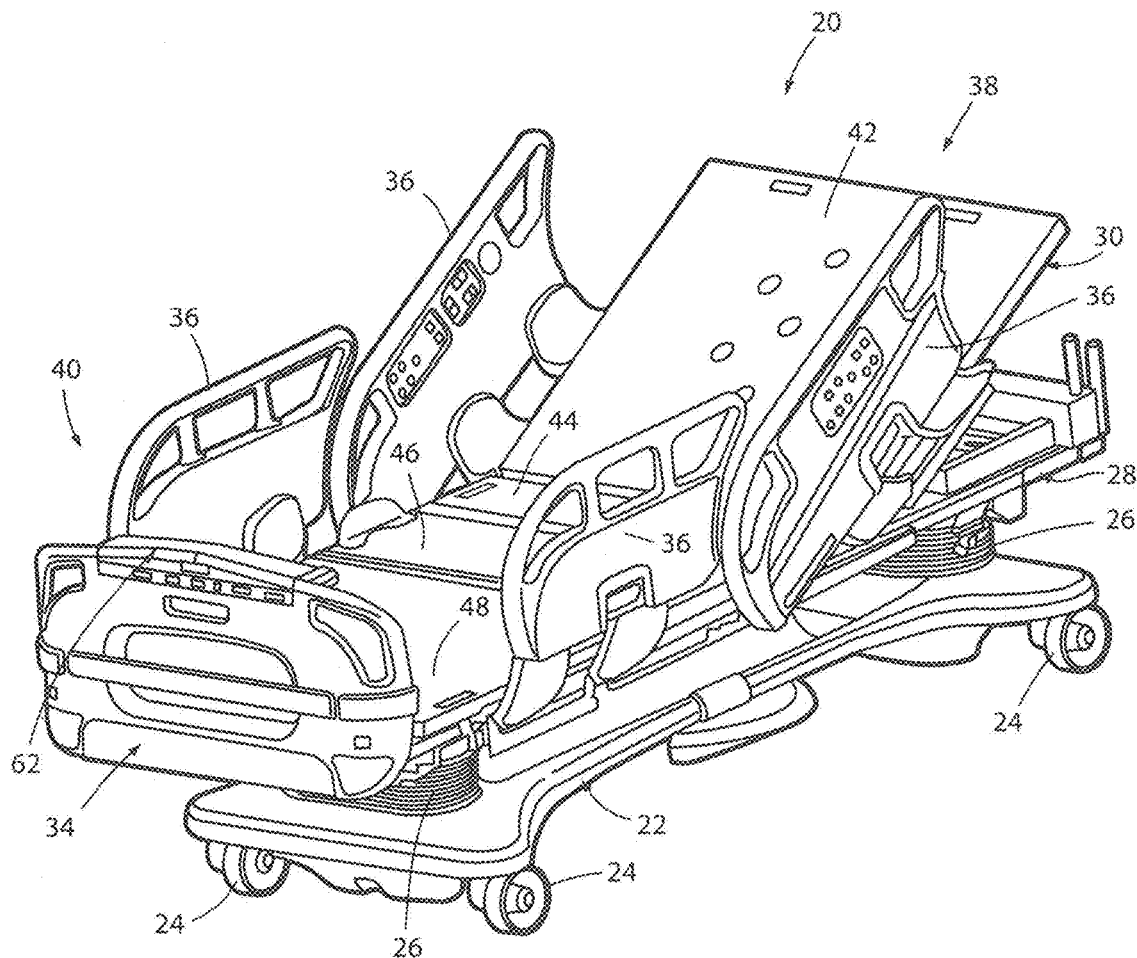
FIG. 1 is a perspective view of a person support apparatus according to one embodiment of the disclosure.

An illustrative person support apparatus 20 that may incorporate one or more aspects of the present disclosure is shown in FIG. 1. Although the particular form of person support apparatus 20 illustrated in FIG. 1 is a bed adapted for use in a hospital or other medical setting, it will be understood that person support apparatus 20 could, in different embodiments, be a cot, a stretcher, a gurney, a recliner, an operating table, a residential bed, or any other structure capable of supporting a person, whether stationary or mobile and/or whether medical or residential.

In general, person support apparatus 20 includes a base 22 having a plurality of wheels 24, a pair of lifts 26 supported on the base, a litter frame 28 supported on the lifts 26, and a support deck 30 supported on the litter frame 28. Person support apparatus 20 further includes a headboard (not shown), a footboard 34, and a plurality of siderails 36. Siderails 36 are all shown in a raised position in FIG. 1 but are each individually movable to a lower position in which ingress into, and egress out of, person support apparatus 20 is not obstructed by the lowered siderails 36. In some embodiments, siderails 36 may be moved to one or more intermediate positions as well.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 38 and a foot end 40, each of whose height can be independently adjusted by the nearest lift 26. Person support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard, footboard 34, and siderails 36. Support deck 30 provides a support surface for a mattress (not shown in FIG. 1), or other soft cushion, so that a person may lie and/or sit thereon. The top surface of the mattress or other cushion forms a support surface for the occupant. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Figure 2:
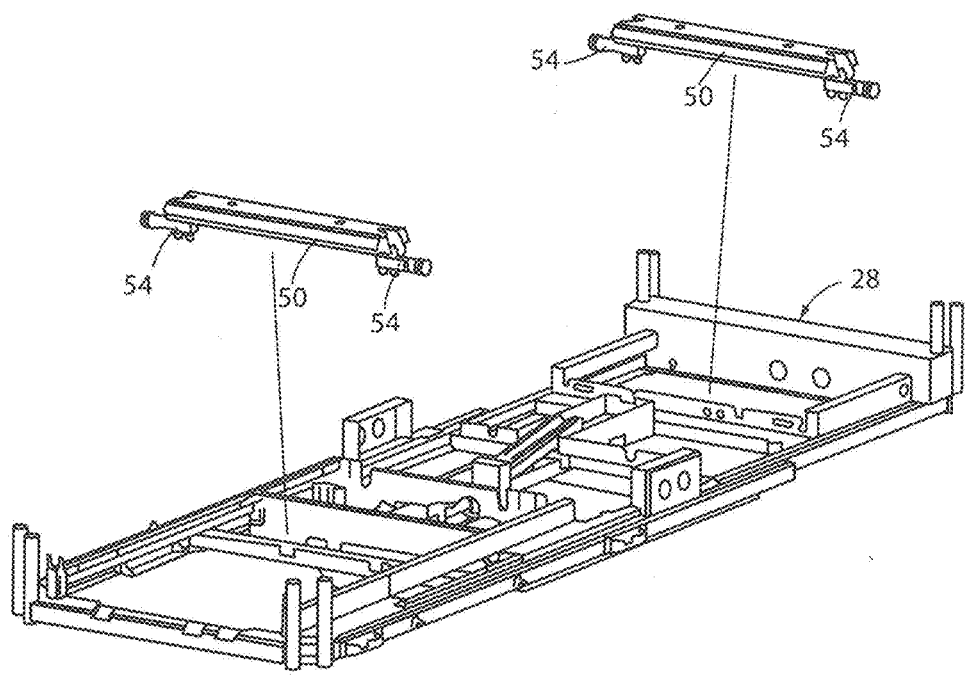
FIG. 2 is a perspective view of a litter frame of the person support apparatus of FIG. 1.
Figure 3:
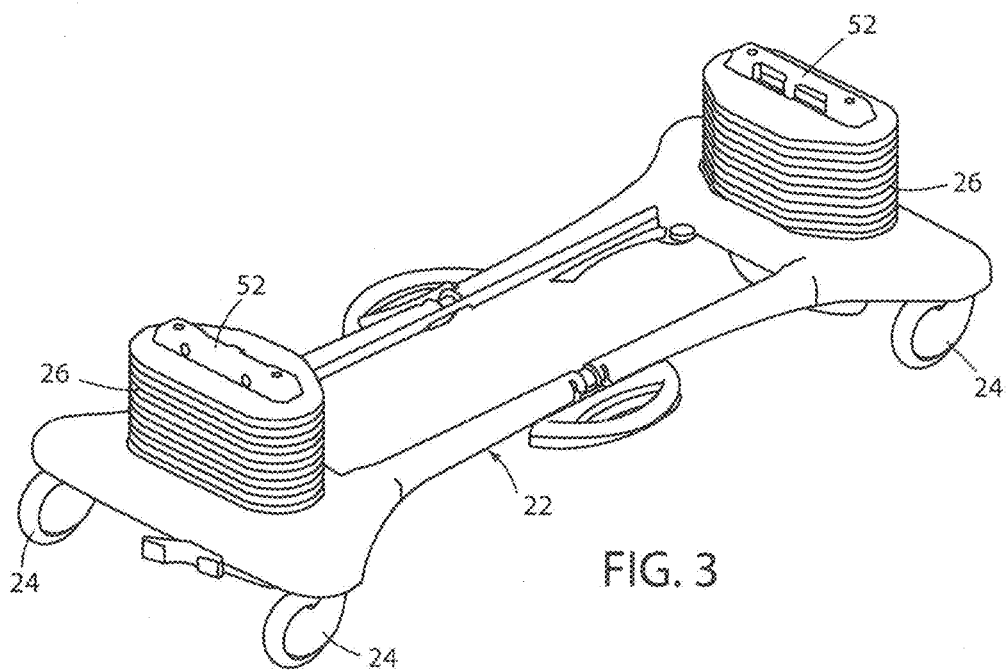
FIG. 3 is a perspective view of a base of the person support apparatus of FIG. 1.

FIG. 2 illustrates in greater detail litter frame 28 separated from lifts 26 and base 22. Litter frame 28 is also shown in FIG. 2 with support deck 30 removed. Litter frame 28 is supported by two lift header assemblies 50. A first one of the lift header assemblies 50 is coupled to a top 52 (FIG. 3) of a first one of the lifts 26, and a second one of the lift header assemblies 50 is coupled to the top 52 of the second one of the lifts 26. Each lift header assembly 50 includes a pair of force sensors 54, which may be load cells, or other types of force sensors, such as, but not limited to, linear variable displacement transducers and/or any one or more capacitive, inductive, and/or resistive transducers that are configured to produce a changing output in response to changes in the force exerted against them.

Although the illustrated embodiment of person support apparatus 20 includes a total of four force sensors 54, it will be understood by those skilled in the art that different numbers of force sensors 54 may be used in accordance with the principles of the present disclosure. Force sensors 54 are configured to support litter frame 28. More specifically, force sensors 54 are configured such that they provide complete and exclusive mechanical support for litter frame 28 and all of the components that are supported on litter frame 28 (e.g. support deck 30, footboard 34, the headboard, siderails 36, etc.). Because of this construction, force sensors 54 are adapted to detect the weight of not only those components of person support apparatus 20 that are supported by litter frame 28 (including litter frame 28 itself), but also any objects or persons who are wholly or partially being supported by support deck 30. The outputs of force sensors 54 are part of an exit detection system described in greater detail below.

The mechanical construction of person support apparatus 20 may be the same as, or nearly the same as, the mechanical construction of the Model 3002 S3 bed manufactured and sold by Stryker Corporation of Kalamazoo, Michigan. This mechanical construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. It will be understood by those skilled in the art that person support apparatus 20 can be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of person support apparatus 20 may also take on forms different from what is disclosed in the aforementioned references.

Figure 4:
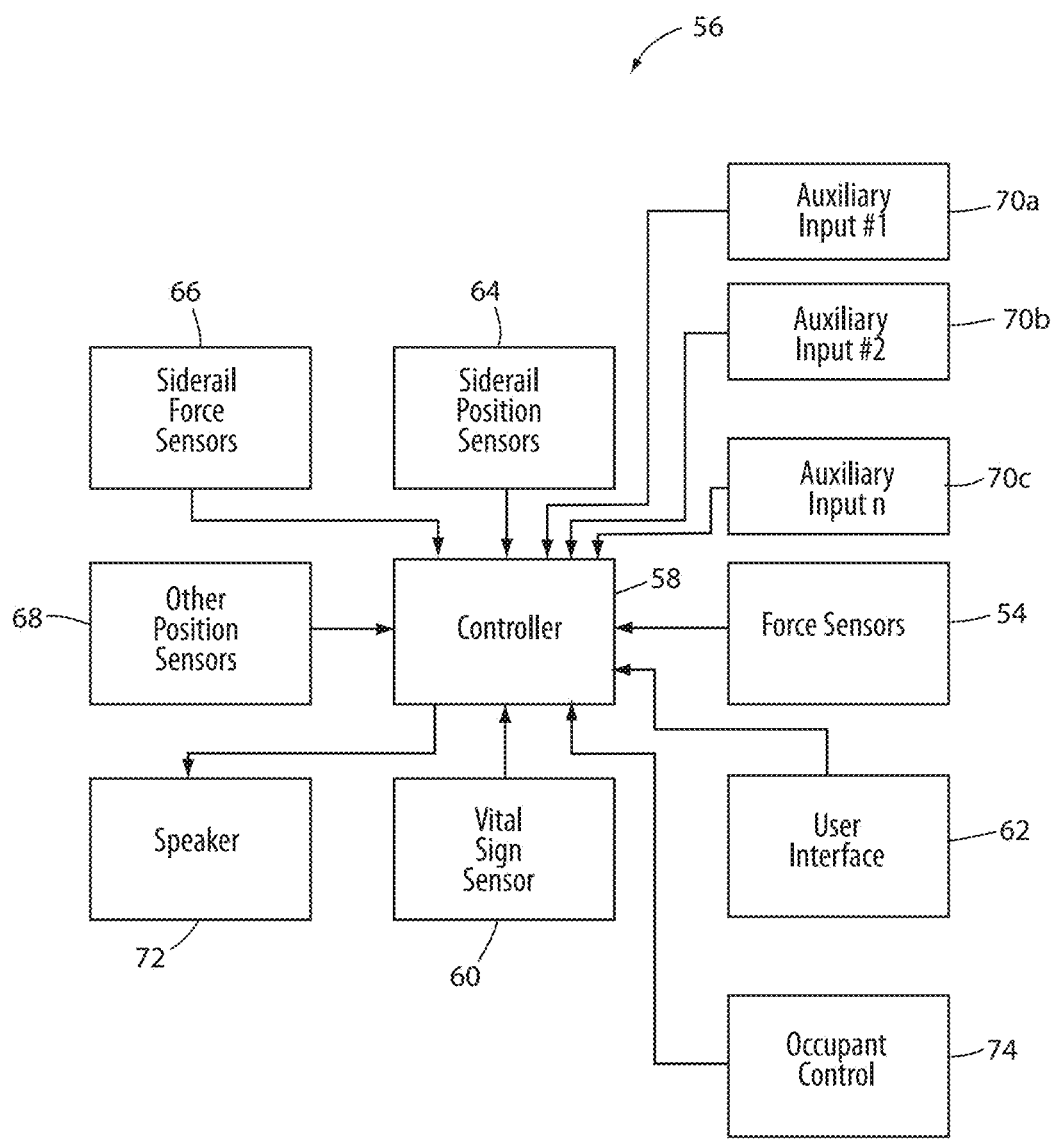
FIG. 4 is a diagram of an exit detection system that may be incorporated into a person support apparatus, such as the person support apparatus of FIG. 1.

As shown more clearly in FIG. 4, person support apparatus 20 includes an exit detection system 56 that is adapted to determine when an occupant, such as, but not limited to, a patient, of person support apparatus 20 is moving and is likely to exit person support apparatus 20. More specifically, exit detection system 56 is adapted to determine when an occupant is moving and is likely to leave prior to the occupant actually leaving, and to issue an alert and/or notification to appropriate personnel so that proper steps can be taken in response to the occupant's imminent departure in a timely fashion. The particular structural details of exit detection system 56 can vary widely. In the embodiment shown in FIG. 4, exit detection system 56 includes force sensors 54, a controller 58, a vital sign sensor 60, a user interface 62, a plurality of siderail position sensors 64, a plurality of siderail force sensors 66, one or more other position sensors 68, a plurality of auxiliary inputs 70, a speaker 72, and an occupant control 74. It will be understood by those skilled in the art, however, that many of the components of exit detection system 56 may be omitted from one or more of the embodiments of exit detection system 56 that are discussed herein. Still further, additional components may be added. These various embodiments are discussed in greater detail below.

Force sensors 54 are adapted to detect downward forces exerted by an occupant of support deck 30. Thus, when an occupant is positioned on support deck 30 and substantially still (i.e. not moving in a manner involving accelerations that cause forces to be exerted against support deck 30), force sensors 54 will detect the weight of the occupant (as well as the weight of any components of person support apparatus 20 that are supported—directly or indirectly—by force sensors 54). Force sensors 54 are also used to determine a center of gravity of the occupant, as will be discussed in greater detail below, in order to determine if the occupant is about to exit person support apparatus 20. In alternative embodiments, the outputs from force sensors 54 are analyzed, not to determine a center of gravity, but instead to determine a weight distribution and/or a change in weight distribution, such as by determining one or more ratios of the relative weights sensed by the force sensors 54 and using them to determine if the occupant is about to exit person support apparatus 20. In still other embodiments, force sensors 54 may be modified to detect forces other than, or in addition to, the downward forces exerted by the occupant. Other types of sensors may also or alternatively be used for determining the occupant's weight.

Controller 58 is constructed of any electrical component, or group of electrical components, that are capable of carrying out the functions described herein. In many embodiments, controller 58 is a conventional microcontroller, although not all such embodiments need include a microcontroller. In general, controller 58 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 58 in carrying out the functions described herein, as well as the data necessary for carrying out these functions, are stored in a memory (not labeled) accessible to controller 58.

Vital sign sensor 60 is a sensor adapted to detect one or more vital signs of the occupant of person support apparatus 20. Such vital signs include, but are not limited to, a respiration rate of the occupant, a breathing rate of the occupant, and a temperature of the occupant. Vital sign sensor 60, in some embodiments, is a non-invasive sensor that detects the occupant's vital signs without requiring the sensor to penetrate the occupant's body. In other embodiments, vital sign sensor 60 may be an invasive sensor.

In at least some embodiments, force sensors 54 are used to detect one or more vital signs of the occupant. Manners for detecting the occupant's vital signs using force sensors 54 are disclosed in commonly assigned U.S. Pat. No. 7,699,784 issued to Wan Fong et al. and entitled SYSTEM AND METHOD FOR MONITORING VITAL SIGNS, the complete disclosure of which is hereby incorporated herein by reference. When forces sensors 54 are to detect one or more of the occupant's vital signs, a separate vital sign sensor 60 may be omitted from exit detection system 56. Alternatively, in some embodiments, force sensors 54 may be used to detect one or more vital signs in combination with the vital sign(s) detected by force sensors 54.

In another alternative embodiment, vital sign sensor 60 comprises one or more accelerometers that are integrated into person support apparatus 20 and used to detect the occupant's heart rate, pulse rate, heart rate variability, and/or breathing rate based upon the vibrations caused by the occupant's heart beat and breathing motions. One manner of using accelerometers for detecting the occupant's heart rate, pulse rate, and/or breathing rate are disclosed in commonly assigned U.S. patent application Ser. No. 62/253,167, filed Nov. 10, 2015, by inventors Marko Kostic et al. and entitled PERSON SUPPORT APPARATUSES WITH ACCELERATION DETECTION, the complete disclosure of which is incorporated herein by reference. Vital signs sensor 60 may also take on any of a variety of different forms. Regardless of its specific form, vital sign sensor 60 reports its output to controller 58 and controller 58 uses its output, in at least some embodiments, to determine whether the occupant is likely to exit person support apparatus 20, as will be discussed in greater detail below.

User interface 62 communicates with controller 58 and enables a user of person support apparatus 20 to control one or more aspects of person support apparatus 20, including exit detection system 56. User interface 62 is implemented in the embodiment shown in FIG. 1 as a control panel having a lid (flipped down in FIG. 1) underneath which is positioned a plurality of controls. The controls—which may be buttons, dials, switches, or other devices—allows a user to control various aspects of exit detection system 56, such as, but not limited to, selecting a mode of operation of exit detection system 56 and/or arming and disarming exit detection system 56. User interface 62 may also include a display for displaying information regarding exit detection system 56. Although FIG. 1 illustrates user interface 62 mounted to footboard 34, it will be understood that user interface 62 can be positioned elsewhere, and/or that one or more additional user interfaces can be added to person support apparatus 20 in different locations, such as the siderails 36, for controlling various aspects of exit detection system 56. In addition, one or more user interfaces may be communicatively coupled to person support apparatus 20 but physically positioned remote from person support apparatus 20, such as, but not limited to, a computer tablet, a smart phone, a computer station, etc.

As noted, user interface 62 includes a control that enables a user to turn exit detection system 56 on and off (arm and disarm exit detection system 56), as well as allowing a user to select different modes which are used for triggering an exit alert, as will be discussed in greater detail below. In at least some embodiments, the controls also allow a user to configure the alerting features of exit detection system 56, including choosing from amongst the different types of alerts that can be issued by exit detection system 56. Such types include local alerts (issued at person support apparatus 20), remote alerts (issued at a remote location, such as a nurse's station, hallway light, or to mobile communication devices carried by personnel), audio alerts, visual alerts, and/or any combinations of these. Still further, user interface 62 allows a user to enter information into exit detection system 56 regarding the occupant (e.g. whether or not the occupant is a fall risk, or what level of fall risk they may be, a gender of the occupant, a height of the occupant, and/or other information); information regarding the environment in which person support apparatus 20 is located (e.g. which side of person support apparatus 20 the occupant may be more liable to exit from, due to proximity to a restroom, hallway, or the layout of the room); and/or other types of information.

Siderail position sensors 64 detect the position of each of the siderails 36. In many embodiments of person support apparatus 20, siderails 36 are movable between a raised position that is intended to prevent the user from exiting person support apparatus 20 at the location of the raised siderail and a lowered position that is out of the way of the occupant, thereby allowing the occupant to exit without the siderail acting as an obstacle to such egress. Siderail sensors 64 report to controller 58 whether each siderail 36 is in the raised or lowered position. In some embodiments of person support apparatus 20, siderails 36 may be movable to one or more intermediate positions that are between the raised and lowered positions. In such embodiments, siderail position sensors 64 also detect which intermediate position the siderails 36 are in and report that to controller 58. As will be discussed in greater detail below, controller 58 uses the siderail position information as a factor, in some embodiments, in determining if the occupant is about to exit from person support apparatus 20. Siderail position sensors 64 may be constructed the same as any conventional siderail position sensors 64, or they may be constructed otherwise.

Siderail force sensors 66 may be included in some embodiments of exit detection system 56. Siderail force sensors 66 detect downward forces that are exerted on siderails 36. Siderail force sensors 66 may therefore be implemented as load cells, or other types of force sensing structures. Siderail force sensors 66 may be included with exit detection system 56 regardless of how siderails 36 are mounted to person support apparatus 20. That is, in some embodiments, siderails 36 are mounted so that the weight of the siderails 36 is not detected by force sensors 54. In such embodiments, siderails 36 are mounted to frame 28, or another structure, at a location where their weight is not supported by force sensors 54. In other embodiments, siderail force sensors 66 are mounted to person support apparatus 20 in a manner such that their weight, as well as any additional downward forces that are exerted on siderail force sensors 66, are detected by force sensors 54. In these latter embodiments, both siderails force sensors 66 and force sensors 54 will detect this additional weight. However, siderail force sensors 66 will not detect weights or other downward forces that are exerted on other parts of the litter frame 28 or deck 30 that are detected by force sensors 54. As will also be discussed in greater detail below, controller 58 uses the siderail forces as a factor, in some embodiments, when determining if the occupant is about to exit from person support apparatus 20.

Position sensor 68 is adapted to detect the position of one or more movable components of person support apparatus 20. In some embodiments, position sensor 68 is adapted to detect an angle of head section 42 (the Fowler section) relative to horizontal (or relative to one or more references on person support apparatus 20 itself). Position sensor 68 may alternatively comprise one or more sensors that detect a height of litter frame 28 relative to base 22. That is, position sensor 68 may alternatively be adapted to detect how far lifts 26 have extended. In still other embodiments, more than one position sensor 68 is included so that, for example, position sensors 68 report both the height of litter frame 28 and the current angle of head section 42 to controller 58. In still other embodiments, the position or orientation of one or more other movable components of person support apparatus 20 are detected and reported to controller 58, either along with one or more of the aforementioned height and Fowler angle, or in lieu of one or both of the height and Fowler angle. In some embodiments, as will be discussed more below, controller 58 uses the position information from the one or more position sensors 68 as a factor in determining if the occupant is about to exit from person support apparatus 20.

Exit detection system 56 may also include one or more auxiliary inputs 70. Auxiliary inputs 70 are constructed as ports into which one or more sensors, cables, or other devices are coupled. The outputs from the sensors, cables, or other devices, are communicated to controller 58 and used as a factor, in some embodiments, in determining if the occupant is about to exit from person support apparatus 20. The number of auxiliary inputs 70 may vary from the number shown in FIG. 4. Indeed, in some embodiments, exit detection system 56 includes no auxiliary inputs 70. However, when one or more auxiliary inputs 70 are included, such auxiliary inputs 70 may be configured in any of the following manners: as a wired port for coupling to a cable (e.g. an Ethernet port for coupling to an Ethernet cable, a USB port for coupling to a USB cable, etc.), as a port for coupling to a wireless transceiver (e.g. a WiFi transceiver, a Bluetooth transceiver, a ZigBee transceiver, a near field communication (NFC) transceiver, etc.), as a port for coupling to one or more additional sensors, and/or as a port for coupling to other devices.

When coupled to an Ethernet cable or a WiFi transceiver, one or more auxiliary inputs 70 may be used to communicate with a healthcare facility computer local area network (LAN). More specifically, inputs 70 may communicate with an Electronic Medical Record (EMR) system that is in communication with the LAN. Such communication may include receiving one or more of the following items of information about the occupant of person support apparatus 20: his or her gender, his or her height and/or weight, his or her fall risk assessment, and/or other information about the occupant. As will be discussed more below, exit detection system 56 uses one or more of these items of information, in some embodiments, as factors in determining whether the occupant is about to exit from person support apparatus 20.

Some embodiments of exit detection system 56 also include speaker 72 and occupant control 74. When so included, exit detection system 56 uses speaker 72 to provide guidance to the occupant of person support apparatus 20 when he or she wishes to exit person support apparatus. As will be discussed in greater detail below, such guidance includes aural instructions that are communicated to the occupant via speaker(s) 72. In some embodiments, exit detection system 56 uses the outputs from one or more sensors, such as, but not limited to, force sensors 54, as feedback for issuing the guidance and/or instructions to the occupant when he or she is exiting person support apparatus 20.

Controller 58 of exit detection system 56 is adapted to determine the center of gravity of the occupant using the outputs from force sensors 54. Controller 58 uses this center of gravity to determine whether or not the occupant is about to exit from person support apparatus 20. In one embodiment, exit detection system 56 determines this center of gravity using the system and method disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. In other embodiments, other algorithms may be used.

Figure 5:
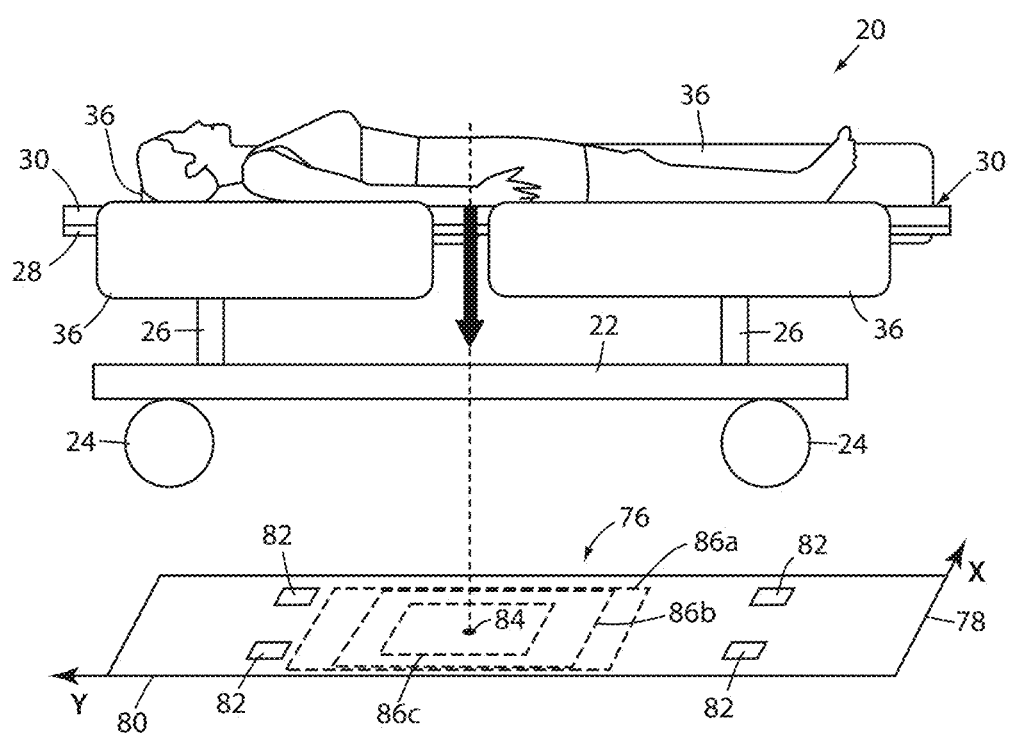
FIG. 5 is a diagram of an illustrative manner in which the exit detection system of FIG. 4 determines if an occupant is about to exit or not.

As shown more clearly in FIG. 5 controller 58 determines the center of gravity of the occupant in a planar coordinate frame of reference, such as reference frame 76. Reference frame 76 includes an X-axis 78 and a Y-axis 80. X-axis 78 is generally parallel to the foot end 40 of person support apparatus 20 while Y-axis 80 is generally parallel to a side of support deck 30. Other coordinate systems can be used. Regardless of which coordinate system is used, controller 58 knows the location of force sensors 54 in the particular coordinate system that is used. In the example shown in FIG. 5, force sensors 54 are shown in known locations 82.

In the illustrative example shown in FIG. 5, controller 58 has determined the occupant's center of gravity to be at a location 84. Controller 58 compares this center of gravity 84 to the active one of zones 86 (i.e. the one selected by the user or caregiver) that are defined in reference frame 76 and determines whether the center of gravity 84 is inside or outside of this active zone 86. If center of gravity 84 moves outside of the active zone 86 (discussed below), controller 58 issues an alert indicating that the occupant is about to exit from person support apparatus 20. When determining whether the center of gravity 84 is outside or inside of the active zone 86, controller 58 may first compute the center of gravity in a first one of the directions of coordinate frame of reference 76 (X direction or Y direction), compare that value to the corresponding boundaries of the zone in that particular direction and, if it is inside the boundaries, compute the center of gravity in the other direction of coordinate frame of reference 76 (X direction or Y direction).

As shown in FIG. 5, there are three different zones 86a, b, and c. Zones 86a, b, and c have different sizes, allowing the occupant to engage in different amounts of movement prior to triggering an exit alert. When exit detection system 56 is in use, a user selects which one of the zones 86a-c will be the active zone using user interface 62. Controller 58 then repetitively recalculates the occupant's center of gravity based upon the outputs from force sensors 54 and compares the calculated center of gravity 84 to the active zone. If the center of gravity 84 is within the active zone 86, no exit alert is issued. If the center of gravity 84 moves outside of the active zone 86, controller 58 issues an alert. In some embodiments, in order to avoid issuing an alert based upon transient weight signals shifting the center of gravity 84 outside of the active zone for a fleeting moment, controller 58 only issues an alert if the center of gravity 84 moves outside of the active zone for more than a threshold amount of time (which may be on the order of seconds or a fraction of a second).

Although FIG. 5 illustrates each zone 86a-c as having a generally rectangular shape, it will be understood that the zones 86a-c do not all have to have the same shape. Further, it will also be understood that any one or more of the zones can be shaped in other manners besides rectangles. In some embodiments, any one or more of the zones 86 are squares, parallelograms, other quadrilaterals, circles, ovals, or any combination of arcs, straight lines, curves, and/or other shapes.

At least one of the zones 86a-c is a zone having a boundary that is dynamic. That is, at least one of the zones 86a-c has a size and/or shape that varies based upon one or more criteria that will be discussed more below. In some embodiments, all of the zones are 86a-c are dynamic. In still other embodiments, exit detection system 56 includes more zones 86 than the three shown in FIG. 5, while in other embodiments, exit detection system 56 includes fewer zones than the three shown in FIG. 5 (including, in some embodiments, only a single dynamic zone 86).

Some of the factors or criteria used by controller 58 to vary the boundary of one or more zones 86 include the following: (a) the weight of the occupant; (b) the height of the occupant; (c) a ratio of the occupant's height and weight; (d) the gender of the occupant; (e) a fall risk assessment of the occupant; (f) values of one or more vital signs of the occupant; (g) a position of the siderails 36; (h) a downward force being applied to one or more of the siderails 36; (i) a position or orientation of one or more other components of person support apparatus 20; (j) the environment or surroundings in which person support apparatus 20 is positioned; (k) a proximity of a caregiver to person support apparatus 20; (l) a time of day; (m) one or more medical conditions of the occupant; (n) a body orientation of the occupant; (o) a current height of litter frame 28, (p) movement of the occupant (e.g. sitting up), and/or other factors. It will be understood that controller 58 is programmed in some embodiments to use only a single one of these factors, while in other embodiments controller 58 is programmed to use any two or more of these of the factors in any possible combination.

In some embodiments of exit detection system 56, the user of person support apparatus 20, such as the caregiver, can use user interface 62 to select the individual factors that are to be used by exit detection system 56, or to select one or more predetermined combinations of factors that are to be used by exit detection system 56 when determining whether to issue an exit alert or not. In other embodiments, the particular combination of factors used by exit detection system 56 is preprogrammed. In still other embodiments, exit detection system 56 includes one or more user-selectable modes in which one or more preprogrammed combinations of factors are used by controller 58 to determine if an exit alert should be issued, but also includes one or more user-selectable modes that allow the user to customize the factors used by controller 58 when determining if an exit alert should be issued or not.

With respect to the weight of the occupant, exit detection system 56 receives this information either directly from force sensors 54 or it is input into exit detection system 56. When input, it may be input via a caregiver entering the weight information via user interface 62, or it may be input by communicating with an EMR system (using one of auxiliary inputs 70). With respect to the height of the occupant, exit detection system 56 receives this information via user interface 62 or from one of auxiliary inputs 70. In some embodiments, a height of the occupant may be automatically detected by way of a pressure sensing mat placed on top of the mattress of person support apparatus 20 (or between the mattress and support deck 30) that communicates with controller 58 (such as via an auxiliary input 70). One such pressure sensing mat suitable for use with exit detection system 56 is disclosed in commonly assigned U.S. patent publication 2014/0039351 filed Mar. 2, 2012, by inventors Joshua Mix et al. and entitled SENSING SYSTEM FOR PATIENT SUPPORTS, the complete disclosure of which is hereby incorporated herein by reference. In other embodiments, the height of the occupant can be detected or approximated using the video and/or thermal imaging technologies disclosed in commonly assigned U.S. patent application Ser. No. 14/578,630 filed Dec. 22, 2014, by inventors Richard Derenne et al. and entitled VIDEO MONITORING SYSTEM, or commonly assigned U.S. patent application Ser. No. 14/692,871 filed Apr. 22, 2015, by inventors Marko Kostic et al. and entitled PERSON SUPPORT APPARATUS WITH POSITION MONITORING, the complete disclosures of both of which are incorporated herein by reference. Still other types of height sensors may alternatively be used.

Regardless of the source of the occupant's height and weight data, controller 58 uses this information to compute an aspect ratio of the occupant. That is, controller 58 uses the height and weight data to compute a ratio of the occupant's height to weight. Controller 58 then adjusts one or more of the boundaries of one or more of the zones 86 based upon this ratio. Specifically, controller 58 adjusts the boundaries of those zone(s) 86 that are dynamic. Those zone(s) 86 that are static do not have their boundaries adjusted.

In one embodiment, controller 58 adjusts the width of a zone 86 based upon the weight and height ratio of the current occupant of person support apparatus 20. The width refers to the size of the zone 86 in the side to side direction (i.e. the horizontal direction perpendicular to the direction running from head end 38 to foot end 40). By adjusting this width, the movement of the occupant's center of gravity 84 in the side-to-side direction will either allow the occupant to move closer to the side of person support apparatus 20 without triggering an exit alert, or it will prevent the occupant from moving as close to the side of the person support apparatus 20 before triggering an exit alert.

In some embodiments, controller 58 extends the width of a zone 86 in response higher weight to height ratios. That is, the heavier an occupant is for a given height, the wider controller 58 makes the width of one or more of the zones 86. In some embodiments, the adjustments to the width of the zone are made incrementally based upon one or more predefined ranges or the occupant's weight to height ratio. For example, weight to height ratios falling anywhere within a first range cause controller 58 to adjust the width of a zone 86 by a first amount, weight to height ratios falling anywhere within a second range cause controller 58 to adjust the width of the zone 86 by a second amount, etc. In some embodiments, only two ranges are used, while in other embodiments, other numbers of ranges are used.

Controller 58 is also programmed in some embodiments to change the height of one or more zones 86 in response to the calculated height to weight ratio of the occupant. In other embodiments, controller 58 only changes the width of a zone 86 in response to different occupant weight to height ratios, or changes both the height and width in response to different weight to height ratios. The height of the zone 86 refers to the length of the zone from its boundary closest to head end 38 to its boundary closest to foot end 40. In some embodiments, controller 58 expands the height of the zone 86 in response to taller occupants (for a given weight) and shrinks the height of zone 86 in response to shorter occupants, while in other embodiments, controller 58 shrinks the height of zone 86 in response to taller occupants and expands the height of zone 86 in response to shorter occupants. As with the width of zones 86, controller 58 may make adjustments to the height in increments based upon ranges of the weight to height ratio.

Controller 58 is also programmed in some embodiments to take into account the gender of the occupant when determining if the occupant is about to exit from person support apparatus 20. Controller 58 is informed of the gender of the occupant from either an auxiliary input 70 (e.g. using an auxiliary input 70 to communicate with and EMR server that includes a medical record for the occupant identifying the gender of the occupant) or from a caregiver, or other user, entering the occupant's gender via user interface 62. Regardless of the source of gender information, controller 58 uses the gender information to adjust the height and/or width of one or more zones 86 based upon an algorithm stored in memory accessible to controller 58. The algorithm is based upon statistical data regarding the common morphology of people of different genders. In some embodiments, the algorithm is based upon statistical data regarding the common morphology of men and women that is also correlated to one or more weight ranges of the men and women.

For example, in some embodiments, controller 58 uses an algorithm that is based on estimations of how far the occupant's center of gravity or weight distribution shifts when men and women of different weights and heights roll from lying on their back to lying on their right or left sides. Such estimates may be made for different height and weight ranges of both men and women. For example, controller 58 may adjust a zone size by a first incremental amount in response to any woman occupying person support apparatus 20 who has a height and/or weight that is within X percent (or a fraction of standard deviations or some other range-defining characteristic) of the median weight and/or height of women (in a particular country or other jurisdiction). In such an example, controller 58 adjusts the zone size by a second incremental amount in response to any woman occupying person support apparatus 20 who has a height and/or weight that is within Y percent (or some other range-defining characteristic) of the median weight and/or height of women, where Y has a different value than X. Still other adjustments may be made to a zone size based upon other height and/or weight ranges for women, as well as still other adjustment that are made for different heights and/or weights of men.

In one embodiment, controller 58 multiplies the zone adjustments discussed above that are made based on the aspect ratio of the occupant (e.g. weight to height, or height to weight) by a first factor if the occupant is male and a second factor if the occupant is female. The different factors account for the typical body morphology differences between males and females, thereby helping to ensure that false exit alerts are reduced while still alerting when the occupant is indeed moving toward exiting person support apparatus 20.

Alternatively, or additionally, controller 58 may account for the gender of the occupant by utilizing one or more pre-stored values for changing the operating threshold(s) of exit detection system 56. The specific pre-stored values that are used for men and women are different. The pre-stored values may be used to define one or more boundaries of the zones 86, or they may be used to define one or more thresholds that are used in determining whether an occupant is exiting or about to exit.

Controller 58 is also programmed in some embodiments to take into account the race or ethnicity of the occupant when determining if the occupant is about to exit from person support apparatus 20. Controller 58 is informed of the race or ethnicity of the occupant from either an auxiliary input 70 (e.g. using an auxiliary input 70 to communicate with and EMR server that includes a medical record for the occupant identifying the race/ethnicity of the occupant) or from a caregiver, or other user, entering the occupant's race/ethnicity via user interface 62. Regardless of the source of this information, controller 58 uses the information to adjust the height and/or width of one or more zones 86 based upon an algorithm stored in memory accessible to controller 58. The algorithm is based upon statistical data regarding the common morphology of people of different races and/or ethnicities.

Controller 58 is also programmed in some embodiments to take into account an assessment of the fall risk of the occupant when determining if the occupant is about to exit from person support apparatus 20. Controller 58 is informed of the fall risk assessment of the occupant from either an auxiliary input 70 (e.g. using an auxiliary input 70 to communicate with and EMR server that includes a medical record for the occupant identifying his or her fall risk) or from a caregiver, or other user, entering the occupant's fall risk via user interface 62. In some instances, controller 58 is programmed to automatically assume a default fall risk if controller 58 is unable to retrieve one from an EMR and/or such information is not entered via user interface 62. In some embodiments, the default fall risk is set to a high risk of falling. Alternatively, or additionally, controller 58 is programmed in some embodiments to calculate a fall risk based upon one or more medical factors of the occupant, such as whether (and/or how recently) surgery was performed on the occupant, whether (and/or how recently) anesthesia was administered to the occupant, and other factors.

Regardless of its source, controller 58 uses the fall risk information to adjust the size of one or more zones 86. In some embodiments, controller 58 shrinks the size of the zone(s) 86 in response to greater fall risks and expands the size of the zone(s) 86 in response to smaller fall risks. In these embodiments, an occupant who is at a high risk of falling will trigger an exit alert with less motion than an occupant who is at a low risk of falling. Other manners of adjusting exit detection system 56 based upon a fall risk assessment are also possible.

Controller 58 is also programmed in some embodiments to take into account readings of one or more vital signs of the occupant when determining if the occupant is about to exit from person support apparatus 20. Controller 58 is informed of the vital sign readings from vital sign sensor 60 and/or one or more vital sign sensors that communicate with controller 58 via one or more auxiliary inputs 70. In some instances, controller 58 is programmed to automatically shrink one or more zones 86 in response to an increase in the occupant's breathing rate, pulse rate, and/or heart rate, and to expand one or more zones 86 in response to a decrease in the occupant's breathing rate, pulse rate, and/or heart rate. Increases in these vital signs are potentially indicative of the occupant intending and/or starting to exit from person support apparatus 20.

In some embodiments, controller 58 may also receive readings from an occupant temperature sensor. In such embodiments, controller 58 uses the temperature readings in determining whether to issue an exit alert or not. For example, in some embodiments, controller 58 expands the size of one or more zones 86 in response to a decrease in the occupant's temperature, such as may occur while the occupant is asleep. In such embodiments, controller 58 reduces the size of the one or more zones 86 in response to an increase in the occupant's temperature, such as may occur when the occupant awakens or is awake. In one of such embodiments, controller 58 communicates with an occupant temperature sensor that includes one or more thermal image sensors having fields of view that include the occupant while positioned on the person support apparatus, such as disclosed in commonly assigned U.S. patent application Ser. No. 14/692,871 filed Apr. 22, 2015, by inventors Marko Kostic et al. and entitled PERSON SUPPORT APPARATUS WITH POSITION MONITORING, the complete disclosure of which is incorporated herein by reference.

Controller 58 is also programmed in some embodiments to take into account the state of the siderails 36 when determining if the occupant is about to exit from person support apparatus 20. Controller 58 is informed of the state of the siderails 36 by siderail position sensors 64. In some instances, controller 58 is programmed to automatically shrink a zone 86 in response to a siderail 36 being in a lowered position such that the siderail does not present a substantial obstacle to the occupant exiting from person support apparatus 20. One example of the manner in which controller 58 may be programmed to respond to different siderail positions is shown in FIGS. 6-8.

Figure 6:
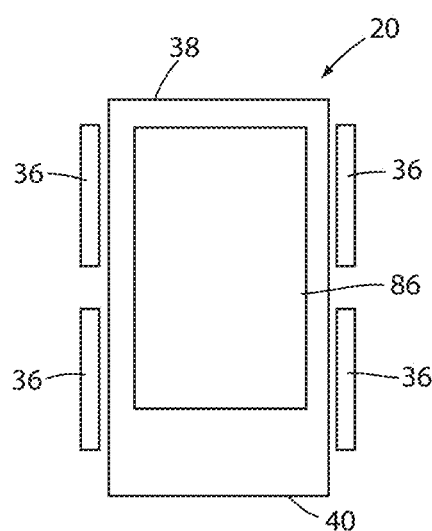
FIG. 6 is a plan view diagram of the person support apparatus illustrating a zone used to trigger an exit alarm shown with all four siderails of the person support apparatus in a raised position.

FIG. 6 illustrates a person support apparatus 20 that has all four siderails 36 in their raised position. As shown, person support apparatus 20 has a zone 86 defined in FIG. 6 that is generally rectangular. When an occupant of person support apparatus 20 moves such that his or her center of gravity 84 travels outside of zone 86, controller 58 issues an alert. FIG. 7 illustrates one manner in which controller 58 adjusts the size of zone 86 in response to the left siderail 36 (in FIG. 7) adjacent the foot end 40 of person support apparatus 20 being moved to a lowered position (and removed from view in FIG. 7). As can be seen in FIG. 7, controller 58 not only shrinks the size of zone 86, but also changes its shape so that the occupant's center of gravity cannot approach the left hand corner of foot end 40 of person support apparatus 20 as closely as it otherwise could (if the siderail were raised) without triggering an exit alert. In other words, if the occupant moves toward a lowered siderail, controller 58 issues an exit alert sooner than it does if the siderail is raised.

Figure 7:
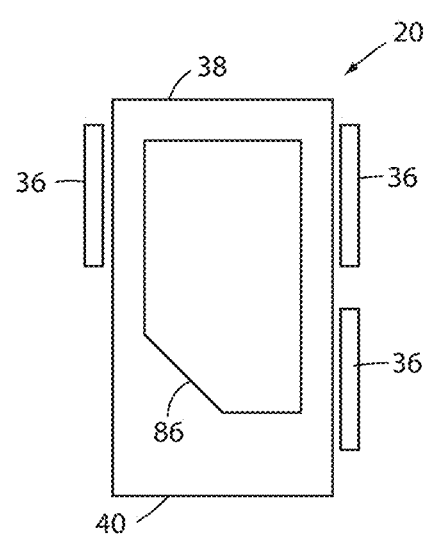
FIG. 7 is a plan view diagram of the person support apparatus of FIG. 6 showing a modification of the zone in response to a siderail being lowered.
Figure 8:
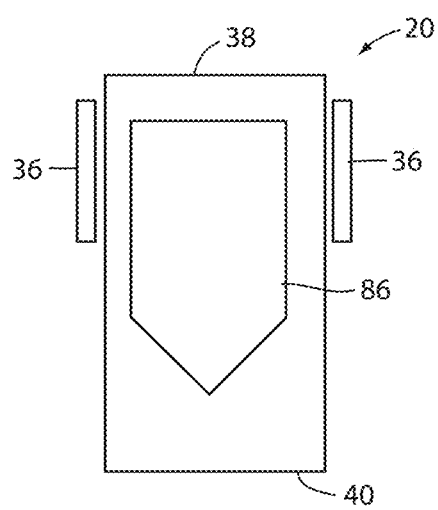
FIG. 8 is a plan view diagram of the person support apparatus of FIG. 6 showing another modification of the zone in response to two siderails being lowered.

FIG. 8 illustrates one manner in which controller 58 further reduces the size of zone 86 in response to both of the foot end siderails 36 being moved to their lowered position. As a result of this change to zone 86, controller 58 issues an exit alert in response to the occupant's center of gravity moving toward the right or left side of foot end 40 of person support apparatus 20 sooner than it would for the siderail configuration of FIG. 6. Although not shown in FIGS. 6-8, controller 58 is further adapted to shrink the size of zone 86 in response to either or both of the siderails 36 adjacent head end 38 being moved to their lowered positions.

Although FIGS. 6-8 illustrate only a single zone 86, it will be understood that, in some embodiments, controller 58 changes the size and shape of multiple zones 86 in response to the raising and lowering of siderails 36. Further, it will be understood that the changes in size and shape illustrated in FIGS. 6-8 are merely one example of the types of changes that may be implemented by controller 58 in response to the movement of the siderails 36. Other types of changes are also possible.

Controller 58 is also programmed in some embodiments to take into account an amount of downward force that is being applied to one or more of the siderails 36 when determining if the occupant is about to exit from person support apparatus 20. Controller 58 is informed of the downward forces exerted on the siderails 36 by siderail force sensors 66. The manner in which controller 58 reacts to the downward forces applied to siderails 36 depends upon the manner in which person support apparatus 20 is constructed to support siderails 36. When constructed in a first manner, siderails 36 are coupled to litter frame 28 and any downward forces that are exerted on siderails 36 are not only detected by siderail force sensors 66, but also by force sensors 54. When constructed in a second manner, siderails 36 are mounted in such a manner that any downward forces that are exerted on siderails 36 are only detected by siderail force sensors 66, and are not detected by force sensors 54. The manner in which controller 58 responds to downward forces on siderails 36 is separately discussed below for these two different constructions.

When person support apparatus 20 is constructed in the first manner (any downward forces on siderails 36 will also be detected by force sensors 54), controller 58 is programmed to distinguish between downward forces on siderails 36 that are likely due to the occupant pushing down on the siderails, and downward forces on siderails 36 that are likely due to a person standing beside person support apparatus 20 and pushing down on siderails 36. When person support apparatus 20 is constructed in this first manner, the occupant's pushing down on a siderail 36 will cause an increase in the force detected by that corresponding siderail force sensor 66, but will not cause an overall increase in the total amount of force detected by force sensors 54. However, if a person standing next to person support apparatus pushes down on a siderail 36, not only will the corresponding siderail force sensor 66 detect this force, but the sum of the forces detected by force sensors 54 will also increase by the amount of the downward force applied by the non-occupant of person support apparatus 20.

Controller 58 is therefore programmed to determine if a force detected by a siderail force sensor 66 is accompanied by a corresponding increase in the sum total of forces detected by force sensors 54. If it is not, controller 58 is programmed to shrink one or more of the zones 86 because the downward forces applied to the siderail 36 are likely due to the occupant and may be indicative of the occupant attempting to climb over the siderail. On the other hand, if the amount of force detected by the siderail force sensor 66 is accompanied by a corresponding increase in the sum total of forces detected by force sensors 54, controller 58 does not change the size of the zone 86 because the forces on the siderail are likely due to a non-occupant person leaning or pushing down on the siderail, which is not indicative of an intent of the occupant to climb over the siderail. In some embodiments, the reduction of the size of zone 86 is only triggered by controller 58 if the downward force on siderail 36 exceeds a threshold.

When person support apparatus 20 is constructed in the second manner where any downward forces detected by sensors 66 are not also detected by force sensors 54, controller 58 is programmed to look at the overall sum of forces detected by force sensors 54 when one or more of the siderail force sensors 66 detects a downward force. If the downward force detected by a siderail force sensor 66 is caused by the occupant pushing down on the siderail, the overall sum of forces detected by force sensors 54 will decrease (due to the occupant shifting part of his or her weight onto the siderail 36 and off of the structure supported by force sensors 54). In such a situation, controller 58 reduces the size of the zone 86 if the downward force detected by sensor 66 exceeds a threshold. On the other hand, if the downward force detected by a siderail force sensor 66 is not accompanied by a corresponding reduction in the sum of forces detected by force sensors 54, then the downward force on the siderail is likely due to a non-occupant person leaning or pushing down on the siderail, which is not indicative of an intent of the occupant to climb over the siderail. In this case, controller 58 does not change the size of zone 86.

Regardless of whether person support apparatus 20 is constructed in the first or second manner, controller 58 is programmed, in some embodiments, to only take into account the forces detected by sensors 66 if the corresponding siderail 36 is in the raised position. In other words, if a siderail force sensor 66 detects a downward force being applied to a particular siderail 36, but that particular siderail 36 is in the lowered position, controller 58 does not change the size or shape of zone 86. This is because, if the siderail is in the down position, controller 58 will have already made a change in the size or shape of the zone 86 in the manner discussed above with respect to FIGS. 6-8, and such a change will typically be sufficient to trigger an exit alert prior to the occupant being able to exert any significant downward force on the lowered siderail. However, if the siderail is in the raised position, controller 58 does use the outputs from the corresponding siderail force sensor 66 to make the changes discussed above to the size and/or shape of zone 86.

Controller 58 is also programmed in some embodiments to take into account the position of one or more other components of person support apparatus 20 when determining if the occupant is about to exit from person support apparatus 20. Controller 58 is informed of the position of one or more other components of person support apparatus 20 by way of one or more of the position sensors 68. Controller 58 adjusts the size and/or shape of one of the zones 86 in response to changes in the position of one or more components (or the occupant) that meet one or more criteria. For example, in one embodiment, controller 58 enlarges the size of a zone in response to the head section 42 being in a flat orientation (or within a threshold angle of the flat orientation), and reduces the size of the zone in response to head section 42 being pivoting upwardly from the flat orientation (or upwardly from the threshold angle). In another example, controller 58 changes the size or shape of the zone in response to changes in the height of litter frame 28 that are caused by lifts 26. In some of these embodiments, controller 58 enlarges the zone 86 in response to one or more height reductions and shrinks the zone in response to one or more height increases. In other embodiments, controller 58 temporarily reduces the zone size in response to lowering the height of litter frame 28 as such lowering may be indicative of an intent by the occupant to imminently exit from person support apparatus 20. Still other changes to one or more zones 86 are possible in light of changes to the angle of head section 42, the height of litter frame 28, and/or the position or orientation of other components of person support apparatus 20.

Controller 58 is also programmed in some embodiments to take into account one or more sequences of movement of the occupant of person support apparatus 20 when determining if the occupant is about to exit from person support apparatus 20. For example, controller 58 may adjust the size and/or shape of a zone 86, or alter other threshold criteria used to determine if an exit alert is to be triggered, based upon the occupant grabbing a siderail 36 for a predetermined amount of time and/or the movement of the occupant's leg or legs off of the side of the person support apparatus 20. Other sequences may be monitored. When taking into account such sequences, controller 58 may rely on sensor data from force sensors 54 and/or other types of sensors, such as, but not limited to, piezo sensors, radar, and/or one or more devices that are communicatively coupled to person support apparatus 20 and that detect quantities associated with movement of the occupant.

Controller 58 is also programmed in some embodiments to take into account the environment of person support apparatus 20 when determining if the occupant is about to exit from person support apparatus 20. Controller 58 is informed of the environment of person support apparatus 20 by a caregiver, or other user, entering environmental information into person support apparatus 20 via user interface 62. In one embodiment, a caregiver uses user interface 62 to instruct controller 58 which side of the person support apparatus 20 is facing toward a restroom. Controller 58 uses this information to adjust the size and/or shape of at least one zone 86 such that movement in that direction is more likely to trigger an exit alert. Controller 58 may also, or alternatively, use this information to adjust the size and/or shape of at least one zone 86 such that movement in the opposite direction is less likely to trigger an exit alert. In general, controller 58 uses this information under the assumption that the occupant is more likely to exit person support apparatus 20 from the side of person support apparatus 20 that is closest to the restroom.

In an alternative embodiment, user interface 62 prompts the caregiver to enter information indicating the caregiver's assessment as to which side of the person support apparatus 20 the occupant is more likely to exit from based upon the current surroundings of the person support apparatus 20. In making this assessment, the user interface 62 may prompt the caregiver to take into account the location of a restroom, the location of a hallway, the location of furniture or other obstacles that may be positioned in the same room as person support apparatus 20, and/or other factors that may indicate which side of person support apparatus 20 the occupant would be more likely to exit from. After receiving this information, controller 58 makes adjustments to one or more of the zones 86 such that movement in the direction corresponding to the greater likelihood of egress triggers an exit alarm sooner, and/or such that movement in the direction corresponding to a lesser likelihood of egress triggers an exit alarm later.

Controller 58 is also programmed in some embodiments to take into account the proximity of a caregiver to person support apparatus 20 when determining if the occupant is about to exit from person support apparatus 20. Controller 58 is informed of the proximity of a caregiver via the addition of a sensor to person support apparatus 20 that detects badges worn by caregivers (when the caregivers are within a defined range of the person support apparatus 20), and/or via information received from another sensor (or set of sensors) that communicates with person support apparatus 20 via one or more of the auxiliary inputs 70.

In the former situation, person support apparatus 20 includes, in some embodiments, an RF ID detector that detects RF signals from badges, or other devices, worn by the caregivers. In the latter situation, person support apparatus 20 communicates with a location and tracking system that, in some embodiments, utilizes RF ID tracking technology. In still other embodiments, person support apparatus 20 communicates with a camera system that provides caregiver location information to controller 58 of person support apparatus 20 via an auxiliary input 70. One such camera system is disclosed in commonly assigned U.S. patent application Ser. No. 14/578,630 filed Dec. 22, 2014, by inventors Richard Derenne et al. and entitled VIDEO MONITORING SYSTEM, the complete disclosure of which is hereby incorporated herein by reference. Still other manners for detecting the proximity of a caregiver to person support apparatus 20 may be used, including, but not limited to, the thermal imaging system disclosed in the previously mentioned Ser. No. 14/692,871 application.

Regardless of the precise manner in which caregiver proximity information is communicated to controller 58, controller 58 uses this information to make an adjustment in the size and/or shape of at least one zone 86 in response to a caregiver being within a threshold distance to person support apparatus 20 (e.g. within the same room) and in response to the caregiver being outside of the threshold distance (e.g. outside of the same room). If the caregiver proximity information is sufficiently granular (i.e. sufficiently precise to know the distance and position of the caregiver relative to person support apparatus 20), controller 58 may also, or alternatively, make changes to the size or shape of at least one zone 86 that takes into account the particular side of person support apparatus 20 that a nearby caregiver is located closest to. Thus, for example, controller 58 may enlarge the portion of the zone 86 that is closest to the caregiver if the caregiver is within a threshold distance of person support apparatus 20. As another example, controller 58 may make changes to the entire shape and/or size of zone 86 based on the distance of the caregiver to person support apparatus, including, but not limited to, changes that vary in response to the distance between the caregiver and person support apparatus 20.

In some embodiments, one or more environmental sensors are included that communicate with person support apparatus 20 and share date regarding the environment in which person support apparatus 20 is currently positioned. Person support apparatus 20 may then use this data to automatically determine which side of person support apparatus 20 the occupant is more likely to exit from. Such environmental sensors may include one or more cameras, three-dimensional scanning devices, ultrasonic time-offlight sensors that "map" the room and determine potential obstacles, and/or still other types of environmental sensors.

Controller 58 is also programmed in some embodiments to take into account the current time when determining if the occupant is about to exit from person support apparatus 20, including, but not limited to, the amount of time that has passed since the occupant last exited from person support apparatus 20. In one such embodiment, controller 58 enlarges one or more zones 86 during evening hours when the occupant is more likely to be sleeping, and reduces one or more zones 86 during the daytime hours when the occupant is more likely to be awake. In another such embodiment, controller 58 reduces one or more zones 86 after a threshold amount of time has passed since the occupant last exited from person support apparatus 20. In such embodiments, the threshold amount of time may be based upon an estimated amount of time that will elapse before the occupant may have to exit the person support apparatus 20 to use the restroom.

In still other time-sensitive embodiments, controller 58 makes an adjustment to the size or shape of at least one of the zones 86 based upon the current time relative to a feeding schedule. In such embodiments, controller 58 may be programmed to take into account the higher likelihood that an occupant may wish to exit person support apparatus 20 after eating or drinking in order to use the restroom. In any of the time-sensitive embodiments, controller 58 may be programmed to enlarge the size of one or more zones 86 in response to the occupant having recently entered person support apparatus 20 (and thus unlikely to exit again soon). Such enlargements are automatically reduced as additional time passes. Still other manners of changing the exit detection system 56 in response to absolute or relative times are possible.

Controller 58 is also programmed in some embodiments to take into account additional information regarding the medical condition of the occupant when determining if the occupant is about to exit from person support apparatus 20. Such additional information may be communicated to controller 58 by a user entering the medical condition information via user interface 62, by communications from an EMR system to person support apparatus 20 via an auxiliary input 70, by one or more sensors (e.g. infrared, ultrasonic, and/or video), or by other means. Such additional medical information includes items such as whether the occupant has recently had surgery, is prone to sleepwalking, has been administered any drugs that may affect his or her stability and/or ability to safety exit person support apparatus 20, has any mental disabilities, his or her age, and/or has any other medical condition that affects his or her ability to safely exit person support apparatus 20. Upon receipt of such information, controller 58 changes one or more of the zones 86 in order to address the increased risk of falling that such information may indicate.

Controller 58 is also programmed in some embodiments to take into account an orientation of the occupant's body when determining if the occupant is about to exit from person support apparatus 20. That is, controller 58 may be programmed to determine if the occupant is sitting up or lying and to change one or more boundaries of one or more zones 86 in response to this determination. One manner in which controller 58 may determine the orientation of the occupant's body is disclosed in commonly assigned U.S. patent application Ser. No. 14/873,734 filed Oct. 2, 2015, by inventors Marko Kostic et al. and entitled PERSON SUPPORT APPARATUS WITH MOTION MONITORING, the complete disclosure of which is incorporated herein by reference. Other manners are disclosed in the commonly assigned U.S. patent application Ser. No. 62/253,167 filed Nov. 10, 2015, which was previously incorporated herein by reference. Still other manners of determining the occupant's orientation may also be used.

Controller 58 is also programmed in some embodiments to take into account one or more outputs from an electromyograph (EMG) when determining if an occupant is about to exit from person support apparatus 20. When so programmed, one or more electromyograph devices are coupled to controller 58 via one or more auxiliary inputs 70. The electromyograph devices deliver electromyogram data regarding the activity of one or more skeletal muscles of the occupant, particularly those of the occupant's legs, although other muscles may be monitored, either in combination with the occupant's legs or separately. The data is derived from one or more surface electrodes coupled to the patient's legs and/or other body areas. Controller 58 analyzes the outputs from the electromyograph device to see if the electrical activity of the occupant's legs, or other muscles, has reached one or more thresholds that are indicative of the level of movement that accompanies exiting from person support apparatus 20. If so, controller 58 alters the size and/or shape of one or more of the exit zones 86.

As mentioned previously, the foregoing examples of the factors that may be used by exit detection system 56 are not necessarily all used in combination with each other. Instead, in some embodiments, exit detection system 56 uses only one of these factors to adjust one or more of the zones 86, while in other embodiments, exit detection system 56 uses a combination of these factors to adjust one or more zones 86. When using multiple factors to adjust exit detection system 56, the different factors may cause changes to the exit detection system at different times and be cumulative to each other. For example, when exit detection system 56 takes into account the gender of the occupant, controller 58 changes an initial size or shape of at least one zone 86 and subsequently uses the adjusted size or shape of that zone as a base zone. Thereafter, further adjustments to the base zone may be made, depending upon the particular factors that controller 58 has been programmed to take into account. For example, if a siderail is lowered, controller 58 then makes an additional adjustment to the base zone. Similarly, if a caregiver approaches within a threshold distance, controller 58 may then make yet another adjustment in addition to the ones previously made. Exit detection system 56 therefore dynamically responds to one or more changing conditions when determining whether an occupant is about to exit from person support apparatus 20 or not.

Although exit detection system 56 has been primarily described herein as computing a center of gravity 84 of the occupant and comparing the position of the computed center of gravity to an active zone 86, it will be understood by those skilled in the art that exit detection system 56 can be modified to process the outputs of force sensors 54 in other manners besides computing a center of gravity. For example, in some embodiments, controller 58 sums the total amount of force on force sensors 54 when person support apparatus 20 is occupied and then looks for shifts of more than a threshold amount of that weight to a side, head end, or foot end of person support apparatus. For example, if a 100 kilogram person is occupying person support apparatus 20, exit detection system 56 may be modified to trigger an exit alert if more than X percent, say, 70 percent ($0.70 \times 100 = 70$ kilograms) of the total forces are detected by the two force sensors 54 positioned along the right side of person support apparatus 20, or by the two force sensors 54 positioned along the left side of person support apparatus 20. In some embodiments, a different ratio of the forces detected by the two force sensors 54 positioned along the foot end 40 of person support apparatus 20 may trigger an exit alert if the ratio exceeds a different threshold, while still another ratio of the forces detected by the two force sensors 54 positioned along the head end 38 of person support apparatus 20 may trigger an exit alert if that ratio exceeds yet a different threshold. In sum, exit detection system 56 can be modified to compute one or more ratios of the force detected by a first force sensor 54 (or the sum of forces detected by a combination of first force sensors 54) to the force, or sum of forces, detected by at least one other force sensor 54. The one or more ratios may then be compared to one or more thresholds for determining whether to issue an exit alert or not. Other types of weight distribution changes may also be used to trigger an exit alert.

When exit detection system 56 is implemented to compute one or more force ratios based on the outputs of force sensors 54 instead of a center of gravity of the occupant, controller 58 modifies the threshold(s) used by exit detection system 56 in response to one or more of the factors discussed above. Thus, for example, exit detection system 56 may be programmed to issue an exit alert if 70 percent of the occupant's weight is detected on the right two force sensors 54 when both of the right siderails 36 are lowered, and to not issue an alert when both of the right siderails are raised until at least 80 percent of the occupant's weight is detected on the right two force sensors. Of course these thresholds are merely illustrative, and different ones may be used.

Further, adjustments may be made to the thresholds used for analyzing the collective outputs of three or more force sensors 54, depending upon the dynamic conditions sensed. For example, if only one of the foot end siderails 36 is lowered and the other three siderails 36 remain raised, controller 58 may be programmed to sum the forces detected by the three force sensors 54 positioned in the three corners other than the one adjacent the lowered siderail and compare that sum to another sum of forces. Alternatively, controller 58 may be programmed to compare the force detected by the force sensor 54 adjacent the lowered siderail to the sum of the forces detected by the other three force sensors 54, or to the total sum detected by all four force sensors. Still other ratios may be calculated.

Further, exit detection system 56 may also be modified to use and analyze the outputs of non-force sensors, either in addition to or in lieu of the outputs from force sensors 54. For example, the principles disclosed herein can be applied to a video image based exit detection system wherein an exit alert is issued if the position of the occupant meets one or more criteria (e.g. the occupant moves to within X distance of a side of person support apparatus 20). Based on one or more of the factors discussed herein (e.g. a siderail being raised or lowered, the occupant's vital signs, etc.), the exit detection system may alter one or more of the criteria (e.g. distance X) based upon these factors. Still other types of exit detection systems may be used in accordance with these principles, including, but not limited to, thermal imaging based exit detection systems, accelerometer based exit detection systems, radar based exit detection systems, pressure sensing exit detection systems, and others.

In addition to detecting when an occupant may be about to exit from person support apparatus 20, exit detection system 56 is also configured, in some embodiments, to provide aural guidance to an occupant when he or she is attempting to exit from person support apparatus 20. In some embodiments, the provision of aural guidance is a feature that may be turned on or off by the caregiver using user interface 62. In other embodiments, this feature is always automatically enabled whenever the exit detection system 56 is not armed. In still other embodiments, this feature automatically disarms or mutes an otherwise armed exit detection system 56 upon the occupant activating one or more occupant controls 74 (FIG. 4).

In some embodiments, when an occupant of person support apparatus 20 wishes to utilize this aural guidance feature, he or she must first activate the occupant control 74. In other embodiments, the aural guidance features is activated automatically when exit detection system 56 detects that the occupant is moving toward exiting person support apparatus 20. In either case, exit detection system 56 issues aural guidance using speaker 72 that helps guide the person when exiting from person support apparatus 20. Such aural guidance includes instructions to slow down when force sensors 54 detect shifts in the occupant's weight that occur faster than a threshold speed. Such aural guidance also includes instructions to change a height of the litter frame 28 to a height more conducive for safe exit if the litter frame 28 is not at that height already. (In some embodiments, the person support apparatus 20 automatically moves to the proper height in response to activation of occupant control 74. Still further, such aural guidance includes instructions for the user to place his or her feet on the ground, to pause for a preset amount of time thereafter, and to subsequently begin shifting his or her weight onto their feet and into a standing position. Additional instructions may also be aurally provided, such as, but not including, instructions to grip and hold a siderail or other secure object for a certain amount of time while transitioning out of person support apparatus 20, hold onto another secure object for a certain amount of time after standing, etc. In addition to aural guidance, video guidance may also be presented.

In still other embodiments, exit detection system 56 communicates with a secondary device worn by the occupant that includes one or more sensors. The sensors may detect one or more vital signs of the occupant, movement of the occupant, and/or other conditions. The secondary device communicates with person support apparatus 20 even when the occupant has exited from person support apparatus 20. In such instances, exit detection system 56 is programmed to change one or more exit detection criteria in response to the data received from the secondary device. The changes to the criteria may occur prior to the occupant returning to the person support apparatus 20 or afterward.

In some embodiments, the exit detection system includes a snooze feature that temporarily disables the alerting function of exit detection system 56. The temporary disablement may last for a predetermined amount of time, or it may be tied to movement of the occupant, which may be monitored by one a secondary device worn by the occupant. Further, in some embodiments, the snooze feature may not disarm the exit detection system 56 completely, but may instead change one or more criteria of the exit detection system 56 temporarily, such as the boundaries of one or more zones 86.

In still other embodiments, exit detection system 56 is programmed to produce and/or send multiple alerts to remote locations based upon the criteria discussed herein. A first one of the multiple alerts is issued when the occupant moves outside of a first zone of the exit detection system 56. A second one is issued if the occupant moves outside of a second zone of exit detection system 56. The first alert is directed specifically to a caregiver assigned to the occupant of person support apparatus 20, while the second alert is sent to a nurse call system of a healthcare facility where it is shared with more than the specific caregiver. The first alert may be local (i.e. within the room in which person support apparatus 20 is located) or it may be remote (i.e. communicated to the caregiver's badge, cell phone, pager, etc.), or a combination of the two. The second alert is forwarded to the existing nurse call system.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A person support apparatus comprising:
a support surface adapted to support thereon an occupant of the person support apparatus; and
an exit detection system adapted to issue an alert if the occupant of the person support apparatus is moving toward exiting the support surface, the exit detection system including a plurality of user-selectable modes, wherein a first mode of the plurality of user-selectable modes takes into account a characteristic of the occupant in determining whether or not the occupant is moving toward exiting the support surface, and wherein a second mode of the plurality of user-selectable modes does not take into account the characteristic of the occupant in determining whether or not the occupant is moving toward exiting the support surface.

2. The person support apparatus of claim 1 wherein the characteristic of the occupant includes at least one of a height, weight, body orientation, vital sign, and fall risk assessment of the occupant.

3. The person support apparatus of claim 1 wherein the exit detection system includes a plurality of force sensors adapted to detect downward forces exerted by the occupant on the support surface, and the exit detection system is further adapted to do the following: (a) to use outputs from the force sensors when operating in both the first mode and the second mode; (b) to allow the user to select a first zone or a second zone as an active zone of the exit detection system; (c) to issue the alert when a variable parameter associated with the detected downward forces indicates the occupant has moved outside a boundary of the active zone; (d) to allow the user to select whether to operate the exit detection system in the first mode with the first zone as the active zone or to operate in the second mode with the second zone as the active zone.

4. The person support apparatus of claim 3 wherein when the exit detection system is operating in the first mode, the exit detection system compares a first value derived from outputs of the force sensors to a first threshold, compares a second value derived from the outputs of the force sensors to a second threshold, and changes at least one of the first and second thresholds in response to the characteristic of the occupant.

5. The person support apparatus of claim 4 wherein the first threshold corresponds to a first boundary related to the support surface and the second threshold corresponds to a second boundary related to the support surface.

6. The person support apparatus of claim 4 wherein the first threshold is derived from a first ratio between a first pair of the force sensors, and the second threshold is derived from a second ratio between a second pair of the force sensors.

7. The person support apparatus of claim 1 further comprising a plurality of siderails movable between raised and lowered positions, and wherein the exit detection system takes into account the position of the siderails when operating in the first mode and determining whether or not the occupant is moving toward exiting the support surface.

8. The person support apparatus of claim 7 wherein the exit detection system also takes into account the position of the siderails when operating in the second mode and determining whether or not the occupant is moving toward exiting the support surface.

9. The person support apparatus of claim 1 wherein the exit detection system is further adapted to perform the following:
to allow the user to select a first zone or a second zone as an active zone of the exit detection system, wherein the exit detection system is adapted to issue the alert when a variable parameter associated with the detected downward forces indicates the occupant has moved outside a boundary of the active zone; and
to allow the user to select whether to operate the exit detection system in the first mode with the first zone as the active zone or to operate in the second mode with the first zone as the active zone.

10. The person support apparatus of claim 9 further comprising a plurality of siderails movable between raised and lowered positions, and wherein the exit detection system takes into account the position of the siderails when operating in both the first mode and the second mode when determining whether or not the occupant is moving toward exiting the support surface.

* * * * *